United States Patent [19]

Pinter

[11] 4,406,885
[45] Sep. 27, 1983

[54] PREPARATION OF NATIVE ONCORNAVIRUS ENVELOPE SUBUNITS AND VACCINES THEREFROM

[75] Inventor: Abraham Pinter, Brooklyn, N.Y.

[73] Assignee: Research Corporation, New York, N.Y.

[21] Appl. No.: 973,958

[22] Filed: Dec. 28, 1978

[51] Int. Cl.$^3$ .................. A61K 39/12; A61K 37/02
[52] U.S. Cl. ...................................... 424/88; 424/89; 424/177
[58] Field of Search ........................... 424/88, 89, 177

[56] References Cited

PUBLICATIONS

Salerno et al. J. Natl. Cancer Inst. 61(6): 1487–1493 Dec. 1978, (Received Mar. 3, 1978, accepted Jul. 23, 1978) Feline Leukemia Virus Envelope Glycoprotein Vaccine: Preparation and Evaluation of Immunizing Potency in Guinea Pig and Cat.
Strand et al. J. Biol. Chem. 251(2): 559–564, Jan. 25, 1976, Structural Protens of Ribonucleic Acid Tumor Viruses:Purification of Envelope, Gore and Internal Components.
De Noronha et al. Virology 85:617–624, (1978) Influence of Antisera to Oncornavirus Glycoprotein (GP71) onInfections of Cats with Feline Leukemia Virus.
Fischinger et al. Virology 71:169–184, (1978) Neutrausation of Homologous and Heterologous Oncornaviruses Against the P15E and GP71 Polcypeptides of Friend Murine Leukemia Virus.
Pinter et al. Virology 83(2):417–422, Dec. 77, The Presence of Disulfide–Linked GP70-P15E Compexes in AKR Murine Leukemia Virus.
Strand et al. Virology 13(1):171–180, Jan. 1974 Structural Proteins of Mammalian Oncogenic RNA Viruses: Multiple Antigenic Determinants of the Major Internal Protein and Envelope Glycoprotein.
Schafer et al. Virology 63:48–59, (1975), Polypeptides of Mammalian Oncornaviruses II. Characterization of a Murine Leukemia Virus Polypeptide (P15) Bearing Interspecies Reactivity.
Ihle et al. Virology 63:60–67, (1975) Polypeptides of Mammalian Oncornaviruses III. Localization of P15 and Reactivity with Natural Antibody.
Ikeda et al. J. Virol. 14(5):1274–1280, Nov. 1974, Biological Expression of Antigenic Determinants of Murine Leukemia Virus Proteins AP69/71 and p. 30.
Famulari et al. J. Virol. 20(2):501–508, Nov. 1976 Presence of Murine Leukemia Virus Envelope Proteins GP70 and p15(E) in a Common Polyprotein of Infected Cells.
Hunsmann et al. Virology 66:327–329, (1975) Properties of Mouse Leukemia Viruses, IX, Active and Passive Immunization of Mice Against Fried Leukemia with Isolated Viral $GP_{71}$ Glycoprotein and its Corresponding Antiserum.
Schafer et al. Javma 158(6):1092–1098, Mar. 15, 1971, A Test System for Identification of the Antigen Shared by Leukemia Viruses of the Cat and other Mammalian Species.

*Primary Examiner*—Shep K. Rose
*Attorney, Agent, or Firm*—Scully, Scott, Murphy & Presser

[57] ABSTRACT

Non-denatured [gp90] is isolated from oncornavirus envelopes including feline and murine leukemia virus envelopes and utilized as vaccines. The materials as isolated may be used directly on in various compositions.

5 Claims, No Drawings

PREPARATION OF NATIVE ONCORNAVIRUS ENVELOPE SUBUNITS AND VACCINES THEREFROM

The invention described herein was made in the course of work under a grant or award from the National Institutes of Health, Education and Welfare.

BACKGROUND OF INVENTION

The most common of all feline hematopoietic cancers, lymphosarcoma (LSA) is known to be caused by an oncornavirus, the feline leukemia virus (FeLV). This virus is also known to cause three other diseases; nonregenerative anemia, a panleukopenia-like syndrome and thymic anemia. It is also associated with, but not yet proved to be the cause of other abnormalities such as myeloproliferative disorders and fetal abortions. It is known the FeLV can grow on the cells of other mammalian species including man and dogs, although it is not clear that the virus is capable of infecting these mammals. Clearly a procedure for protecting against infection by FeLV would be of great value.

It has been observed that some cats can develop immunity to FeLV infections. The development of an effective vaccine, therefore, has appeared to be possible. There are four possible types of FeLV vaccines. These are (a) those consisting primarily of live attenuated FeLV, (b) those consisting of killed FeLV, (c) those produced from cells infected with FeLV, and (d) those composed of FeLV subunits.

U.S. Pat. No. 4,034,081 is based on a divisional application of the application which resulted in the issuance of U.S. Pat. No. 3,966,907. Both patents describe vaccines based on virus which are killed, for example, by irradiation, hydroxylamine, or paraformaldehyde; or inactivated, for example by mitomycin D. The patents also describe vaccines based on cells infected with FeLV.

Oncornaviruses such as murine leukemia virus (MuLV) Rausher and Friend strains, R-MuLV and F-uLV as well as FeLV are known to contain two outer envelope subunits. These are: (1) a glycoprotein with an approximate molecular weight of 70,000 daltons, and (2) a nonglycosylated protein with an approximate molecular weight of 15,000 daltons. These are commonly designated gp70 and p15 (E). The former subunit has also been referred to as gp71; see Fischinger et al, Virology 71, 169 (1976) and Noranha et al, Virology 85, 617 (1978).

The individual subunits gp70 and p15 (E) have been utilized to produce antisera to FeLV and MuLV in goats and this antisera has been utilized to produce passive immunity to FeLV in cats, see Fischinger et al and Noronha et al infra. No vaccines for FeLV capable of producing long term effects based on viral subunits have yet been described.

THE INVENTION

A procedure has now been discovered for the isolation of [gp90] in good yield and without denaturation. This isolate is useful as a vaccine to establish long term production in cats against infection by FeLV.

Generally speaking, the procedure for the isolation of [gp90] involves an initial treatment of the virus particles or virions with a chemical activating agent to form a disulfide bond between gp70 and p15 (E). The disulfide complex which is [gp90] is then isolated from the treated virions. The first step is disruption of the viral envelope with an aqueous mixture of a nonionic detergent at a high salt concentration using, for example, a soluble alkali or alkaline earth metal salt. The resulting mixture containing the lysed virus is then centrifuged on sucrose gradients prepared in a buffer containing a small amount of nonionic detergent. After high speed centrifugation, [gp90] bands in the gradient while other viral proteins either remain at the top or pellet at the bottom of the tube. Homogeneous preparations containing non-denatured [gp90] can be obtained by factionation of the gradient. The fractions containing [gp90] can be utilized directly as a vaccine. Alternatively, [gp90] can be isolated after dialysis against water, by freeze drying.

Useful activating agents include, for example, N-ethylmaleimide (NEM) and dithiobis (m-nitropyridine) (DTNP). Other conventional activating agents of the class known to oxidize sulfhydryl groups on proteins and form disulfide links may also be employed. Typically in order to effect reaction, a suspension of the virus particles, preferably purified, in saline solution is treated with a dilute solution containing an excess of the selected activating agent and allowed to stand for ten to sixty minutes at selected temperatures from 0° C. to 40° C., preferably at ambient temperature, i.e., 20° C. to 35° C.

An excess of the reagent may be employed, but too large an excess should be avoided so as to minimize the possibilities for side reactions.

Typically, the viral suspension will contain from 1 to 10 mg/ml of virus particles, preferably 4 to 6 mg/ml, and the concentration of reagent will be from 0.01% to 1% by weight. The reaction mixture will normally contain viral suspension and reagent in a volume ratio of from 0.5 to 1:0.05 to 0.1. As a genral rule highly dilute suspensions, solutions or mixtures are to be avoided since the concentration of the resulting vaccine will be too low for practical use. On the other hand, high concentrations may result in purification difficulties.

At the end of the reaction period, the viral envelope is disrupted by treatment with the selected nonionic detergent and the selected salt. Although a wide variety of such detergents can be employed, the preferred nonionic detergent is NP-40, which is available from the Shell Development Corporation. The preferred salt is sodium chloride. The concentration ranges are 0.05% to 10% by weight and 0.25 M to 2.0 M respectively.

The mixture is allowed to stand at ambient temperature for from ten to sixty minutes to complete the lysis of the virions. The resulting solution contains the [gp90] complexed to the nonionic detergent. It also contains other solutes including core components and other envelope units. The [gp90] is separated on a sucrose gradient by centrifugation.

The sucrose gradient solution is prepared in the conventional manner with the gradient running from 10% to 25% sucrose on a weight per volume basis. The sucrose solution additionally contains TN buffer and 0.1% by weight of nonionic detergent, preferably the same detergent used for viral disruption. TN buffer is 0.01 M tris-0.10 M sodium chloride. Other conventional buffers such as phosphate buffered saline may be employed.

The lysed mixture is then subjected to high speed centrifugation at from 125,000 g to 150,000 g for from 16 to 24 hours, or equivalent conditions. The gradient is then fractionated. Typically, the non-denatured [gp90] appears in the middle fractions, at a concentration of from about 50 to 100 μg/ml. Of course, the exact fractions in which it will appear depends upon the centrifugal forces applied and the time period.

The [gp90] in the sucrose gradient moves with a mobility that is equivalent to that of a chemically cross-linked complex of gp70 and p15 (E) which has been shown by SDS-PAGE to have a molecular weight of from about 360,000 to 450,000 daltons suggesting that it exists in the gradient as a complex with the detergent.

The fractions which contain the [gp90] can be used directly as a vaccine. When about 1 ml to 2 ml of the fraction is injected intramuscularly into a cat, it will generate a high antibody titer in the serum and will establish a long lasting immunity to FeLV in the cat. Better results are obtained if the treatment is repeated three or four times at monthly intervals.

While it is preferred not to do so, because it adds extra steps, the [gp90] as separated in the fraction, can be isolated, for example, by freeze drying after dialysis. The residue can be taken up in sterilized isotonic solution containing appropriate solutes such as sodium chloride or glucose, and the solution used as a vaccine in exactly the same manner as the sucrose gradient fractions.

It is presently believed the [gp90] in the sucrose gradient is a tetramer comprising four units, each unit composed of gp70 linked to p15 (E) by a covalent bond. The tetramer is complexed with the nonionic detergent, and the complex has a molecular weight of from 360,000 to 450,000.

The product [gp90] can be immunoprecipitated with anti-gp70 and anti-p15 (E) sera, clearly indicating the presence of both of these components in the molecule.

When the complex of [gp90] and detergent is subjected to sodium dodecyl sulfate polyacrylamide gel electrophoresis (SDS-PAGE) its mobility is consistent with a molecular weight of approximately 90,000 daltons.

The product [gp90] is a glycoprotein as shown by the facts that (a) is is labeled when the virus is grown in the presence of carbohydrate precursors such as tritiated glucosamine, (b) it is labeled following treatment of the virions with galactose oxidase followed by reduction with tritiated sodium borohydride. This is consistent with the presence of gp70 in [gp90] since the former is known to be a glycoprotein. Additionally, labeled gp70 is obtained when labeled [gp90] is reduced with mercaptoethanol.

MuLV is also an oncornavirus. Its chemical structure is very similar to that of FeLV. The gp70 from MuLV has been shown to have antigenic determinants in common with gp70 from FeLV. Furthermore, p15 (E) subunits from the two viruses appear to be strongly related. It contains gp70 and p15 (E) subunits similar to these same subunits in FeLV. It is also possible to isolate a non-denatured [gp90] from the viral envelope of MuLV using the process described above. This product may be used as a vaccine. This product is antigenically similar to [gp90] from FeLV in many respects. It appears that a [gp90] is common to, or can be isolated from most mammalian leukemia viruses and that useful vaccines can be prepared from them.

Structural studies of the type described above and illustrated in the examples can be carried out with both the denatured and non-denatured form of [gp90] with the same results. The principal benefits of this invention, however, is that non-denatured [gp90] can be isolated and used as a vaccine or in a vaccine composition.

As illustrated in Example 2, [gp90] can also be isolated by chromatographic procedures. The particular absorbent illustrated in the example is phosphocellulose.

Another form of vacine based on [gp90] which is within the scope of this invention is one in which a [gp90] is administered to the mammal to be protected in the form of a virosome. To prepare vaccines of this nature, [gp90] is incorporated into liposomes and the resulting [gp90] containing products can be used as vaccines.

In the procedure for preparing the virosomes of this invention, [gp90] is isolated either by the centrifugation procedure of the phosphocellulose procedure described above, and illustrated in the examples, except that NP-40 in either the sucrose gradient or the buffer is replaced by a dialyzable nonionic detergent such as β-D-octylglucoside. Egg lecithin solubilized with the dialyzable detergent is added to the [gp90] containing fractions obtained by either of the two principal procedures in a sufficient amount so that the lipid-protein ratio is 1:1 (w/w). The detergent is removed by dialysis against an appropriate buffer such as PBS. The resulting composition is one in which [gp90] is incorporated into a micellar lipid bilayer. It can be used directly as a vacine.

What has been described are methods of isolating virus subunits either in pure form, or in compositions which are directly useful as vaccines. Either the pure subunits or the compositions can be further compounded with conventional adjuvants. In any event the products described are useful for administration to mammals to protect against diseases caused by feline leukemia virus. The invention is illustrated by the following non-limiting examples:

EXAMPLE 1

Isolation of [gp90] from FeLV using NEM

A suspension of FeLV in 0.9 ml TN buffer, at a concentration of 5 mg/ml, is treated with 0.1 ml of 1% solution of NEM in TN buffer (prepared by diluting a stock solution of 10% w/v of NEM in acetonitrile 1:10 with TN buffer), for 15 minutes at room temperature. The solution is then adjusted to 0.5% NP-40 and 0.5 M NaCl by adding 0.125 mls of 5% NP-40 and 5 M NaCl, and the virus is lysed by incubation at 37° C. for 15 minutes. [gp90] is then isolated from the viral lysate by centrifugation on NP-40 containing sucrose gradients.

The sample (~1.2 mls) is placed on top of a preformed linear gradient composed of ~6 mls of 25% sucrose and 6 mls of 10% sucrose prepared in a buffer consisting of TN containing 0.1% NP-40, formed in a Beckman SW-41 centrifuge tube (with the dense solution at the bottom of the tube and the less dense solution at the top). After centrifugation at ~150,000 g (35,000 rpm) at 4° C. for at least 18 hours, the gradient is fractionated into 1 ml fractions. Aliquots of each fraction are analyzed by SDS-PAGE, and the gel is then stained to determine which fraction contains [gp90]. Under the conditions described, [gp90] is located in fractions containing ~15% sucrose.

EXAMPLE 2

Isolation of [gp90] from FeLV using phosphocellulose

After treatment with NEM, the virus suspension is dialyzed against 1 liter of 0.01 M N,N-bis (2-hydroxyethyl)-2-aminoethane sulfonic acid (BES) which had been adjusted to a pH of 6.5 with NaOH. The solution is then treated with 1/10 volume of 10% NP-40 at 37° C. for 15 minutes following which the solution is vigorously vortexed and then clarified by a low speed spin (3,000 rpm for 15' in a Beckman table top centrifuge). The supernatant is then applied to a column containing approximately 1 ml of phosphocellulose which had been washed in 0.01 M BES buffer containing 0.1% NP-40 and 10% sucrose (Buffer A). After the sample enters the column, the column is washed with 1 ml of Buffer A, and developed with a 16 ml linear gradient composed of 8 mls Buffer A and 8 mls of 0.01 M BES+0.1% NP-40+0.7 M NaCl. 1 ml fractions are collected, and 0.050 ml aliquots are analyzed by SDS-PAGE to determine the fractions containing [gp90]. The [gp90] elutes at a salt concentration of ~0.1 to 0.3 M NaCl.

EXAMPLE 3

Isolation of [gp90] from FeLV using DTNP

The procedure used is as described above, except that in place of NEM, the virus is treated with 0.1 ml of a solution of 0.2% dithiobis-m-nitropyridine in dimethyl sulfoxide, for 15 minutes at room temperature.

EXAMPLE 4

Isolation of [gp90] from MuLV using either NEM or DTNP

The proceudres is exactly as described in examples 1 and 2, except that MuLV is used in place of FeLV.

EXAMPLE 5

Structural studies of [gp90]

A. Reduction of [gp90] with mercaptoethanol and identification of gp70 and p15 (E) in the reaction mixture.

A sample of ~0.050 ml of purified [gp90] is treated with 0.0055 mls of 10% SDS and 10% mercaptoethanol in water at 100° for 2 minutes. The sample is then analyzed by SDS-PAGE and components with the mobilities of gp70 and p15 (E) are detected.

B. Use of SDS-PAGE with [gp90] to establish molecular weight.

A sample containing [gp90] is analyzed by SDS-PAGE on 7.5% acrylamide slab gel using the buffer system of Laemmli (*Nature* (*London* ) 277, 680–685, 1970). Adjacent lanes contain the following protein standards—phosphorylase BSA, catalase, which have known molecular weights of 94,000, 67,000 and 60,000 daltons. A plot of mobility versus log molecular weight is drawn for the protein markers, and this graph is used to determine the molecular weight of [gp90] from its mobility. The molecular weight is about 90,000.

C. Immunoprecipitation of [gp90] with anti-gp70 and anti-p15 (E) sera.

A virus sample uniformly labelled with $^{14}C$-amino acids, containing [gp90], is lysed by the addition of NP-40 and NaCl to a final concentration of 0.5% and 0.5 M, diluted to 0.200 mls with RIP buffer (0.01 M Tris, 0.5% NP-40, 0.5 M NaCl) and then incubated with 0.005 mls of either monospecific anti-gp70, anti-p15 (E), or normal goat serum at 37° for one hour. The solution is then shaken with 0.025 mls of a 10% suspension of stabilized Staph A (Pansorbin, Calbiochem) for 5 minutes, then the Staph A is pelleted by centrifugation at 3,000 rpm for 10 minutes. The pellets are washed with 10 mls of high salt buffer (0.01 M Tris, 0.5% NP-40, 1.0 M NaCl), then with 10 mls of low salt buffer (0.002% Tris, 0.5% NP-40) and the washed pellet finally resuspended in 0.010 ml of TN containing 1% SDS and incubated at 100° for 2 minutes. The Staph A is then pelleted out and the supernatant, containing the immunoprecipitated proteins, is analyzed by SDS-PAGE.

EXAMPLE 6

Use of [gp90] from FeLV as a vaccine

The [gp90] purified as described above is used to immunize young cats. 0.10–1.0 mls of purified [gp90] containing approximately 5 μg of protein is mixed with an equal volume of complete Freund's adjuvant and injected i.p. into cats. Immunizations are repeated as above at monthly intervals, except that after the first immunization, incomplete Freund's adjuvant is used. The animals are test bled one and two weeks after each vaccination and the serum is tested for precipitating and neutralizing antibodies using both a lysed virus radioimmunoprecipitation assay and a virus netralization assay with FeLV. It is found that a stable and effective antibody titer can be established and maintained.

What is claimed is:

1. A non-denatured glycoprotein, [gp90] having a molecular weight of 90,000 daltons, comprised of units of gp70 and p15 (E), capable of immunoprecipitation with anti-gp70 sera and anti-p15 (E) sera, yielding gp70 and p15 (E) upon reduction with mercaptoethanol, which is aqueous solution in the presence of nonionic detergents exists as a complex with a molecular weight of 360,000 to 450,000.

2. A vaccine to protect cats against infection by feline leukemia virus containing the glycoprotein [gp90] as its principal active ingredient.

3. A vaccine as in claim 2 wherein the [gp90] is obtained from feline leukemia virus.

4. A vaccine as in claim 2 wherein the [gp90] is obtained from murine leukemia virus.

5. A method for protecting cats against disease caused by feline leukemia virus which comprises administering to a cat a vaccine containing the glycoprotein [gp90].

* * * * *